(12) United States Patent
Defossa et al.

(10) Patent No.: US 7,795,445 B2
(45) Date of Patent: Sep. 14, 2010

(54) SUBSTITUTED 2-AMINOALKYLTHIOBENZIMIDAZOLE COMPOUNDS, PHARMACEUTICAL COMPOSITIONS THEREOF AND METHODS FOR THEIR USE

(75) Inventors: Elisabeth Defossa, Frankfurt am Main (DE); Karl Schoenafinger, Frankfurt am Main (DE); Gerhard Jaehne, Frankfurt am Main (DE); Christian Buning, Frankfurt am Main (DE); Georg Tschank, Frankfurt am Main (DE); Ulrich Werner, Frankfurt am Main (DE)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 11/855,221

(22) Filed: Sep. 14, 2007

(65) Prior Publication Data

US 2008/0090889 A1 Apr. 17, 2008

Related U.S. Application Data

(63) Continuation of application No. PCT/EP2006/003000, filed on Apr. 1, 2006.

(30) Foreign Application Priority Data

Apr. 16, 2005 (DE) .................. 10 2005 017 605

(51) Int. Cl.
*A61K 31/4184* (2006.01)
*C07D 235/28* (2006.01)
(52) U.S. Cl. .................................... 548/307.1; 514/387

(58) Field of Classification Search ............... 548/307.1
See application file for complete search history.

(56) References Cited

FOREIGN PATENT DOCUMENTS

| JP | 36-010978 B4 * | 7/1961 |
| WO | WO 2005/021536 | 3/2005 |

OTHER PUBLICATIONS

Nakajima et al., CA 58:81542, 1963.*

* cited by examiner

*Primary Examiner*—Laura L. Stockton
(74) *Attorney, Agent, or Firm*—Serena Farquharson-Torres

(57) ABSTRACT

The present invention comprises the substituted 2-aminoalkylthiobenzimidazoles of formula I

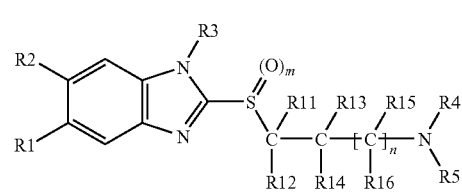

wherein R1-R5 and R11-R16 are hereinafter defined. These compounds, their derivatives and the pharmaceutically acceptable salts thereof are useful in the reduction of elevated blood sugar levels and are therefore useful in the treatment of hyperglycemia, diabetes, atherosclerosis and other blood sugar disorders. These compounds are particularly suitable in the treatment of type-2 diabetes.

4 Claims, No Drawings

SUBSTITUTED 2-AMINOALKYLTHIOBENZIMIDAZOLE COMPOUNDS, PHARMACEUTICAL COMPOSITIONS THEREOF AND METHODS FOR THEIR USE

CROSS-REFERENCE TO RELATED APPLICATIONS

This application is a continuation of International Patent Application No. PCT/EP2006/003000 filed on Apr. 1, 2006 which is incorporated herein by reference in its entirety which also claims the benefit of priority of German patent application Ser. No. 10/2005017605.4 filed on Apr. 16, 2005.

FIELD OF THE INVENTION

The present invention relates generally to pharmaceutical compounds and compositions comprising them for the treatment of metabolic blood serum disorders and the physiological manifestations thereof. More specifically, the present invention relates to pharmaceutical compounds and compositions comprising them for the treatment of metabolic blood glucose disorders such as diabetes, hypoglycemia, hyperglycemia, hyperlipidemia, hypercholesterolemia and the like. More specifically, the present invention relates to substituted 2-aminoalkylthiobenzimidazoles, functional derivatives thereof, their pharmaceutically acceptable salts and pharmaceutical compositions comprising them.

BACKGROUND OF THE INVENTION

The present invention comprises the use of substituted 2-aminoalkylthiobenzimidazoles, functional derivatives thereof, their pharmaceutically acceptable salts and pharmaceutical compositions comprising them.

and their physiologically compatible salts thereof for producing a pharmaceutical composition for the treatment of blood sugar disorders. These compounds are particularly useful in the reduction of blood sugar and, more specifically, in the therapeutic treatment of diabetes. The use of related or similar compounds has been known and described in the prior art as set forth in EP 1 122 257 and EP 0 392 317.

SUMMARY OF THE INVENTION

The present invention comprises the substituted 2-aminoalkylthiobenzimidazoles of formula I

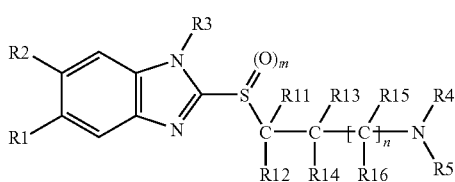

I wherein R1-R5 and R11-R16 are hereinafter defined. These compounds, their derivatives and the pharmaceutically acceptable salts thereof are useful in the reduction of elevated blood sugar levels and are therefore useful in the treatment of hyperglycemia, diabetes, atherosclerosis and other blood sugar disorders. These compounds are particularly suitable in the treatment of type-2 diabetes.

DETAILED DESCRIPTION OF THE INVENTION

The present invention relates to the substituted 2-aminoalkylthiobenzimidazoles compounds of formula I, below:

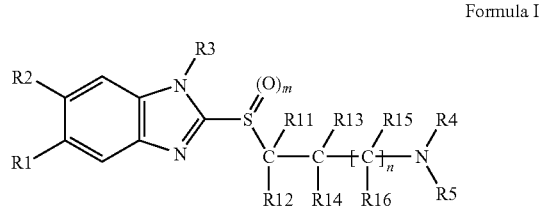

Formula I wherein:
R1 and R2 are each independently selected from the group consisting of H, CONR20R21, NR22COR23 and NR24R25, with the stipulation that the R1 and R2 substituents cannot both be hydrogen;

R20 is selected from the group consisting of $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl and $(C_1-C_6)$-alkylene-$(C_6-C_{10})$-heterocycle, wherein the alkyl, cycloalkyl, alkenyl, alkynyl, alkylene, aryl and heterocycle radicals may be mono- or poly-substituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl or $S(O)_2$—$(C_1-C_6)$-alkyl;

R21 is selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl and $(C_1-C_6)$-alkylene-$(C_6-C_{10})$-heterocycle, wherein the alkyl, cycloalkyl, alkenyl, alkynyl, alkylene, aryl and heterocycle radicals may be mono- or poly-substituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl or $S(O)_2$—$(C_1-C_6)$-alkyl;

R22 and R23 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle or $S(O)_2$-aryl, wherein the alkyl, cycloalkyl, alkenyl, alkynyl, aryl and heterocycle radicals may be mono- or poly-substituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl or $S(O)_2$—$(C_1-C_6)$-alkyl;

R24 is selected from the group consisting of $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle or $S(O)_2$-aryl, wherein the alkyl, cycloalkyl, alkenyl, alkynyl, alkylene, aryl and heterocycle radicals may be mono- or poly-substituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl or $S(O)_2$—$(C_1-C_6)$-alkyl;

R25 is selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle and $S(O)_2$-aryl, wherein the alkyl, cycloalkyl, alkenyl, alkynyl, alkylene, aryl and heterocycle radicals may be mono- or poly-substituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl or $S(O)_2$—$(C_1-C_6)$-alkyl;

R3 is selected from the group consisting of $CF_3$, $(C_2-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, wherein the alkyl, cycloalkyl, alkenyl, alkynyl, aryl and heterocycle radicals may be mono- or poly-substituted by F, Cl, Br, I, CN, $NO_2$, SH, OH, $(C_1-C_6)$-alkyl, —$CF_3$, —$OCF_3$, —$SCF_3$, $(C_2-C_6)$-alkenyl, $(C_2-C_6)$-alkynyl, OR7, OP(O)(OR7)$_2$, NR7R8, NR7CONR7R8, COR7, OCOR7, OCOOR7, COOR7, CONR7R8, OCONR7R8, $(C_1-C_6)$-alkylene-OR7, $(C_1-C_6)$-alkylene-NR7R8, $(C_1-C_6)$-alkylene-NR7S(O)$_2$R7, $(C_1-C_6)$-alkylene-SR7, $(C_1-C_6)$-alkylene-S(O)R7, $(C_1-C_6)$-alkylene-S(O)$_2$R7, $(C_1-C_6)$-alkylene-S(O)$_2$NR7R8, $(C_1-C_6)$-alkylene-COR7, $(C_1-C_6)$-alkylene-COOR7, $(C_1-C_6)$-alkylene-CONR7R8, SR7, S(O)R7, S(O)$_2$R7, S(O)$_2$NR7R8, NR7S(O)$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl or heterocycle;

with the stipulation that R3 cannot be unsubstituted or substituted piperidin-4-yl or unsubstituted or substituted —$CH_2$—$(C_6H_4)$—$(C_6H_5)$.

R7 and R8 are each independently selected from the group consisting of H, $(C_1-C_6)$-alkyl, —$CF_3$, $(C_3-C_{10})$-cycloalkyl, $(C_6-C_{10})$-aryl, heterocycle, $(C_1-C_6)$-alkylene-CONR9R10, CONR9R10, $(C_1-C_6)$-alkylene-COOR9, COOR9, COR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S(O)$_2$R9, S(O)R9, S(O)$_2$R9, $(C_1-C_4)$-alkylene-$(C_6-C_{10})$-aryl and $(C_1-C_4)$-alkylene-heterocycle;

R9 and R10 are each independently selected from the group consisting of H, $(C_1-C_6)$-alkyl, $(C_1-C_6)$-alkylene-$(C_6-C_{10})$-aryl, —$(C_6-C_{10})$-aryl, heterocycle and $(C_1-C_6)$-alkylene-heterocycle;

R4 and R5 are each independently selected from the group consisting of H, $(C_1-C_6)$-alkyl or $(C_3-C_8)$-cycloalkyl, wherein $(C_1-C_6)$-alkyl or $(C_3-C_8)$-cycloalkyl may be substituted by F, Cl, Br, I, CN, aryl, heterocycle, $NH_2$, NH($C_1-C_6$)-alkyl, N(($C_1-C_6$)-alkyl)$_2$, OH, O($C_1-C_6$)-alkyl, O-aryl, O-heteroaryl, S($C_1-C_6$)-alkyl, S(O)($C_1-C_6$)-alkyl or S(O)$_2$($C_1-C_6$)-alkyl, wherein these alkyl groups may in turn be substituted by F, Cl, Br or I;

R11, R12, R13, R14, R15 and R16 are each independently selected from the group consisting of H, $(C_1-C_6)$-alkyl, aryl, heterocycle, $(C_3-C_8)$-cycloalkyl, $(C_1-C_4)$-alkylene-O—$(C_1-C_6)$-alkyl, $(C_1-C_4)$-alkylene-S—$(C_1-C_6)$-alkyl, $(C_1-C_4)$-alkylene-NH—$(C_1-C_6)$-alkyl, $(C_1-C_4)$-alkylene-N(alkyl)$_2$, $(C_1-C_4)$-alkylen-$(C_6-C_{10})$-aryl, $(C_1-C_4)$-alkylene-heterocycle, F, Cl, Br, I, CN, COOH, COO($C_1-C_6$)-alkyl, $CONH_2$, CONH($C_1-C_6$)-alkyl, CON(($C_1-C_6$)-alkyl)$_2$, $CF_3$, or, two of the R11, R12, R13, R14, R15, R16 substituents together form a $(C_2-C_6)$-alkylene group which may be fused to a $(C_6-C_{10})$-aryl substituent or a $(C_6-C_{10})$-heterocycle radical, and these aryl or heterocycle radicals may be substituted by F, Cl, Br, I, $OCF_3$, $CF_3$, CN, $(C_1-C_6)$-alkyl, aryl, heterocycle, $(C_3-C_8)$-cycloalkyl, $(C_1-C_4)$-alkylene-O—$(C_1-C_6)$-alkyl, $(C_1-C_4)$-alkylene-S—$(C_1-C_6)$-alkyl, $(C_1-C_4)$-alkylene-NH—$(C_1-C_6)$-alkyl, $(C_1-C_4)$-alkylene-N(($C_1-C_6$)-alkyl)$_2$, $(C_1-C_4)$-alkylene-$(C_6-C_{10})$-aryl, $(C_1-C_4)$-alkylene-heterocycle, COOH, COO($C_1-C_6$)-alkyl, $CONH_2$, CONH($C_1-C_6$)-alkyl, CON(($C_1-C_6$)-alkyl)$_2$, OH, O—$(C_1-C_6)$-alkyl, O—$(C_3-C_6)$-cycloalkyl, S—$(C_1-C_6)$-alkyl, S—$(C_3-C_6)$-cycloalkyl, SO—$(C_1-C_6)$-alkyl, SO—$(C_3-C_6)$-cycloalkyl, $SO_2$—$(C_1-C_6)$-alkyl, $SO_2$—$(C_3-C_6)$-cycloalkyl, $SO_2$—$NH_2$, $SO_2$—NH—$(C_1-C_6)$-alkyl and $SO_2$—NH—$(C_3-C_7)$-cycloalkyl;

m is 0, 1 or 2;

n is 0 or 1;

and the pharmaceutically acceptable salts thereof.

Preferably, compounds of the present invention comprise compounds of formula I in which one or more of the R-groups are each defined as follows:

R1 and R2 are each independently selected from the group consisting of H, NR22COR23 and NR24R25, wherein the two R1 and R2 substituents cannot both be hydrogen;

R22 and R23 are each independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle or S(O)$_2$-aryl, wherein the alkyl, cycloalkyl, alkenyl, alkynyl, alkylene, aryl and heterocycle substituents may be mono- or poly-substituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl and S(O)$_2$—$(C_1-C_6)$-alkyl;

R24 is selected from the group consisting of $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle or S(O)$_2$-aryl, wherein the alkyl, cycloalkyl, alkenyl, alkynyl, alkylene, aryl and heterocycle groups may be mono- or poly-substituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl or S(O)$_2$—$(C_1-C_6)$-alkyl;

R25 is selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, $(C_1-C_6)$-alkylene-$(C_6-C_{10})$-aryl, $(C_1-C_6)$-alkylene-$(C_6-C_{10})$-heterocycle and S(O)$_2$-aryl, wherein the alkyl, cycloalkyl, alkenyl, alkynyl, alkylene, aryl and heterocycle groups may be mono- or poly-substituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl or S(O)$_2$—$(C_1-C_6)$-alkyl;

R3 is selected from the group consisting of $CF_3$, $(C_2-C_{10})$-alkyl, $(C_3-C_{10})$-cycloalkyl, $(C_2-C_{10})$-alkenyl, $(C_2-C_{10})$-alkynyl, $(C_6-C_{10})$-aryl, heterocycle, wherein the alkyl, cycloalkyl, alkenyl, alkynyl, aryl and heterocycle substituents may be mono- or poly-substituted by F, Cl, Br, I, CN, $NO_2$, SH, OH, $(C_1-C_6)$-alkyl, —$CF_3$, —$OCF_3$, —$SCF_3$, $(C_2-C_6)$-alkenyl, $(C_2-C_6)$-alkynyl, OR7, OP(O)(OR7)$_2$, NR7R8, NR7CONR7R8, COR7, OCOR7, OCOOR7, COOR7, CONR7R8, OCONR7R8, $(C_1-C_6)$-alkylene-OR7, $(C_1-C_6)$-alkylene-NR7R8, $(C_1-C_6)$-alkylene-NR7S(O)$_2$R7, $(C_1-C_6)$-alkylene-SR7, $(C_1-C_6)$-alkylene-S(O)R7, $(C_1-C_6)$-alkylene-S(O)$_2$R7, $(C_1-C_6)$-alkylene-S(O)$_2$NR7R8, $(C_1-C_6)$-alkylene-COR7, $(C_1-C_6)$-alkylene-COOR7, $(C_1-C_6)$-alkylene-CONR7R8, SR7, S(O)R7, S(O)$_2$R7, S(O)$_2$NR7R8, NR7S(O)$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl and $(C_6-C_{10})$-heterocycle;

with the stipulation that R3 cannot be unsubstituted or substituted piperidin-4-yl or unsubstituted or substituted —$CH_2$—$(C_6H_4)$—$(C_6H_5)$.

R7 and R8 are each independently selected from the group consisting of H, $(C_1-C_6)$-alkyl, —$CF_3$, $(C_3-C_{10})$-cycloalkyl, $(C_6-C_{10})$-aryl, heterocycle, $(C_1-C_6)$-alkylene-CONR9R10, CONR9R10, $(C_1-C_6)$-alkylene-COOR9, COOR9, COR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S (O)$_2$R9, S(O)R9, S(O)$_2$R9, (C$_1$-C$_4$)-alkylene-(C$_6$-C$_{10}$)-aryl and (C$_1$-C$_4$)-alkylene-heterocycle;

R9 and R10 are each independently selected from the group consisting of H, (C$_1$-C$_6$)-alkyl, (C$_1$-C$_6$)-alkylene-(C$_6$-C$_{10}$)-aryl, —(C$_6$-C$_{10}$)-aryl, heterocycle or (C$_1$-C$_6$)-alkylene-heterocycle;

R4 and R5 are each independently selected from the group consisting of H, (C$_1$-C$_6$)-alkyl or (C$_3$-C$_8$)-cycloalkyl, wherein (C$_1$-C$_6$)-alkyl or (C$_3$-C$_8$)-cycloalkyl may be substituted by F, Cl, Br, I, CN, aryl, heterocycle, NH$_2$, NH(C$_1$-C$_6$)-alkyl, N((C$_1$-C$_6$)-alkyl)$_2$, OH, O(C$_1$-C$_6$)-alkyl, O-aryl, O-heteroaryl, S(C$_1$-C$_6$)-alkyl, S(O)(C$_1$-C$_6$)-alkyl or S(O)$_2$(C$_1$-C$_6$)-alkyl, wherein these alkyl groups may in turn be substituted by F, Cl, Br or I;

R11, R12, R13, R14, R15 and R16 are each independently selected from the group consisting of H, (C$_1$-C$_6$)-alkyl, (C$_1$-C$_6$)-aryl, (C$_1$-C$_6$)-heterocycle, (C$_3$-C$_8$)-cycloalkyl, (C$_1$-C$_4$)-alkylene-O—(C$_1$-C$_6$)-alkyl, (C$_1$-C$_4$)-alkylene-S—(C$_1$-C$_6$)-alkyl, (C$_1$-C$_4$)-alkylene-NH—(C$_1$-C$_6$)-alkyl, (C$_1$-C$_4$)-alkylene-N(alkyl)$_2$, (C$_1$-C$_4$)-alkylen-(C$_6$-C$_{10}$)-aryl, (C$_1$-C$_4$)-alkylene-heterocycle, F, Cl, Br, I, CN, COOH, COO(C$_1$-C$_6$)-alkyl, CONH$_2$, CONH(C$_1$-C$_6$)-alkyl, CON((C$_1$-C$_6$)-alkyl)$_2$, CF$_3$, or, two of the R11, R12, R13, R14, R15 and R16 substituents together form a (C$_2$-C$_6$)-alkylene group which may be fused to a (C$_6$-C$_{10}$)-aryl group or a (C$_6$-C$_{10}$)-heterocycle group and these aryl or heterocycle groups may be substituted by F, Cl, Br, I, OCF$_3$, CF$_3$, CN, (C$_1$-C$_6$)-alkyl, aryl, heterocycle, (C$_3$-C$_8$)-cycloalkyl, (C$_1$-C$_4$)-alkylene-O—(C$_1$-C$_6$)-alkyl, (C$_1$-C$_4$)-alkylene-S—(C$_1$-C$_6$)-alkyl, (C$_1$-C$_4$)-alkylene-NH—(C$_1$-C$_6$)-alkyl, (C$_1$-C$_4$)-alkylene-N((C$_1$-C$_6$)-alkyl)$_2$, (C$_1$-C$_4$)-alkylene-(C$_6$-C$_{10}$)-aryl, (C$_1$-C$_4$)-alkylene-heterocycle, COOH, COO(C$_1$-C$_6$)-alkyl, CONH$_2$, CONH(C$_1$-C$_6$)-alkyl, CON((C$_1$-C$_6$)-alkyl)$_2$, OH, O—(C$_1$-C$_6$)-alkyl, O—(C$_3$-C$_6$)-cycloalkyl, S—(C$_1$-C$_6$)-alkyl, S—(C$_3$-C$_6$)-cycloalkyl, SO—(C$_1$-C$_6$)-alkyl, SO—(C$_3$-C$_6$)-cycloalkyl, SO$_2$—(C$_1$-C$_6$)-alkyl, SO$_2$—(C$_3$-C$_6$)-cycloalkyl, SO$_2$—NH$_2$, SO$_2$—NH—(C$_1$-C$_6$)-alkyl and SO$_2$—NH—(C$_3$-C$_7$)-cycloalkyl;

m is 0, 1 or 2;
n is 0 or 1;

and the pharmaceutically acceptable salts thereof.

More preferably, compounds of the present invention are compounds of formula I in which one or more substituents are defined as follows:

R1 is H;
R2 is NR22COR23 or NR24R25;
R22 and R23 are each independently H selected from the group consisting of (C$_1$-C$_{10}$)-alkyl, (C$_3$-C$_{10}$)-cycloalkyl, (C$_2$-C$_{10}$)-alkenyl, (C$_2$-C$_{10}$)-alkynyl, (C$_6$-C$_{10}$)-aryl, heterocycle, (C$_1$-C$_6$)-alkylene-(C$_6$-C$_{10}$)-aryl, (C$_1$-C$_6$)-alkylene-(C$_6$-C$_{10}$)-heterocycle or S(O)$_2$-aryl, wherein the alkyl, cycloalkyl, alkenyl, alkynyl, alkylene, aryl and heterocycle radicals may be mono- or poly-substituted by F, Cl, Br, I, CN, NO$_2$, SH, OH, (C$_1$-C$_6$)-alkyl, O—(C$_1$-C$_6$)-alkyl, S—(C$_1$-C$_6$)-alkyl, S(O)—(C$_1$-C$_6$)-alkyl and S(O)$_2$—(C$_1$-C$_6$)-alkyl;

R24 is selected from the group consisting of (C$_1$-C$_{10}$)-alkyl, (C$_3$-C$_{10}$)-cycloalkyl, (C$_2$-C$_{10}$)-alkenyl, (C$_2$-C$_{10}$)-alkynyl, (C$_6$-C$_{10}$)-aryl, heterocycle, (C$_1$-C$_6$)-alkylene-(C$_6$-C$_{10}$)-aryl, (C$_1$-C$_6$)-alkylene-(C$_6$-C$_{10}$)-heterocycle or S(O)$_2$-aryl, wherein the alkyl, cycloalkyl, alkenyl, alkynyl, alkylene, aryl and heterocycle groups may be mono- or poly-substituted by F, Cl, Br, I, CN, NO$_2$, SH, OH, (C$_1$-C$_6$)-alkyl, O—(C$_1$-C$_6$)-alkyl, S—(C$_1$-C$_6$)-alkyl, S(O)—(C$_1$-C$_6$)-alkyl and S(O)$_2$—(C$_1$-C$_6$)-alkyl;

R25 is selected from the group consisting of H, (C$_1$-C$_{10}$)-alkyl, (C$_3$-C$_{10}$)-cycloalkyl, (C$_2$-C$_{10}$)-alkenyl, (C$_2$-C$_{10}$)-alkynyl, (C$_6$-C$_{10}$)-aryl, heterocycle, (C$_1$-C$_6$)-alkylene-(C$_6$-C$_{10}$)-aryl, (C$_1$-C$_6$)-alkylene-(C$_6$-C$_{10}$)-heterocycle or S(O)$_2$-aryl, wherein the alkyl, cycloalkyl, alkenyl, alkynyl, alkylene, aryl and heterocycle radicals may be mono- or poly-substituted by F, Cl, Br, I, CN, NO$_2$, SH, OH, (C$_1$-C$_6$)-alkyl, O—(C$_1$-C$_6$)-alkyl, S—(C$_1$-C$_6$)-alkyl, S(O)—(C$_1$-C$_6$)-alkyl or S(O)$_2$—(C$_1$-C$_6$)-alkyl;

R3 is selected from the group consisting of CF$_3$, (C$_2$-C$_{10}$)-alkyl, (C$_3$-C$_{10}$)-cycloalkyl, (C$_2$-C$_{10}$)-alkenyl, (C$_2$-C$_{10}$)-alkynyl, (C$_6$-C$_{10}$)-aryl, heterocycle, wherein the alkyl, cycloalkyl, alkenyl, alkynyl, aryl and heterocycle radicals may be mono- or poly-substituted by F, Cl, Br, I, CN, NO$_2$, SH, OH, (C$_1$-C$_6$)-alkyl, —CF$_3$, —OCF$_3$, —SCF$_3$, (C$_2$-C$_6$)-alkenyl, (C$_2$-C$_6$)-alkynyl, OR7, OP(O)(OR7)$_2$, NR7R8, NR7CONR7R8, COR7, OCOR7, OCOOR7, COOR7, CONR7R8, OCONR7R8, (C$_1$-C$_6$)-alkylene-OR7, (C$_1$-C$_6$)-alkylene-NR7R8, (C$_1$-C$_6$)-alkylene-NR7S(O)$_2$R7, (C$_1$-C$_6$)-alkylene-SR7, (C$_1$-C$_6$)-alkylene-S(O)R7, (C$_1$-C$_6$)-alkylene-S(O)$_2$R7, (C$_1$-C$_6$)-alkylene-S(O)$_2$NR7R8, (C$_1$-C$_6$)-alkylene-COR7, (C$_1$-C$_6$)-alkylene-COOR7, (C$_1$-C$_6$)-alkylene-CONR7R8, SR7, S(O)R7, S(O)$_2$R7, S(O)$_2$NR7R8, NR7S(O)$_2$R7, (C$_1$-C$_6$)-alkylene-(C$_3$-C$_{10}$)-cycloalkyl, (C$_1$-C$_6$)-alkylene-(C$_6$-C$_{10}$)-aryl, (C$_1$-C$_6$)-alkylene-heterocycle, (C$_3$-C$_{10}$)-cycloalkyl, (C$_6$-C$_{10}$)-aryl and heterocycle;

with the stipulation that R3 cannot be unsubstituted or substituted piperidin-4-yl or unsubstituted or substituted —CH$_2$—(C$_6$H$_4$)—(C$_6$H$_5$).

R7 and R8 are each independently H, (C$_1$-C$_6$)-alkyl, —CF$_3$, (C$_3$-C$_{10}$)-cycloalkyl, (C$_6$-C$_{10}$)-aryl, heterocycle, (C$_1$-C$_6$)-alkylene-CONR9R10, CONR9R10, (C$_1$-C$_6$)-alkylene-COOR9, COOR9, COR9, (C$_1$-C$_6$)-alkylene-COR9, (C$_1$-C$_6$)-alkylene-OR9, (C$_1$-C$_6$)-alkylene-NR9R10, (C$_1$-C$_6$)-alkylene-SR9, (C$_1$-C$_6$)-alkylene-S(O)R9, (C$_1$-C$_6$)-alkylene-S(O)$_2$R9, S(O)R9, S(O)$_2$R9, (C$_1$-C$_4$)-alkylene-(C$_6$-C$_{10}$)-aryl and (C$_1$-C$_4$)-alkylene-heterocycle;

R9 and R10 are each independently H, (C$_1$-C$_6$)-alkyl, (C$_1$-C$_6$)-alkylene-(C$_6$-C$_{10}$)-aryl, —(C$_6$-C$_{10}$)-aryl, heterocycle and (C$_1$-C$_6$)-alkylene-heterocycle;

R4 and R5 are each independently H, (C$_1$-C$_6$)-alkyl or (C$_3$-C$_8$)-cycloalkyl, wherein (C$_1$-C$_6$)-alkyl or (C$_3$-C$_8$)-cycloalkyl may be substituted by F, Cl, Br, I, CN, aryl, heterocycle, NH$_2$, NH(C$_1$-C$_6$)-alkyl, N((C$_1$-C$_6$)-alkyl)$_2$, OH, O(C$_1$-C$_6$)-alkyl, O-aryl, O-heteroaryl, S(C$_1$-C$_6$)-alkyl, S(O)(C$_1$-C$_6$)-alkyl and S(O)$_2$(C$_1$-C$_6$)-alkyl, wherein these alkyl groups may in turn be substituted by F, Cl, Br or I;

R11, R12, R13, R14, R15 and R16 are each independently H, (C$_1$-C$_6$)-alkyl, aryl, heterocycle, (C$_3$-C$_8$)-cycloalkyl, (C$_1$-C$_4$)-alkylene-O—(C$_1$-C$_6$)-alkyl, (C$_1$-C$_4$)-alkylene-S—(C$_1$-C$_6$)-alkyl, (C$_1$-C$_4$)-alkylene-NH—(C$_1$-C$_6$)-alkyl, (C$_1$-C$_4$)-alkylene-N(alkyl)$_2$, (C$_1$-C$_4$)-alkylen-(C$_6$-C$_{10}$)-aryl, (C$_1$-C$_4$)-alkylene-heterocycle, F, Cl, Br, I, CN, COOH, COO(C$_1$-C$_6$)-alkyl, CONH$_2$, CONH(C$_1$-C$_6$)-alkyl, CON((C$_1$-C$_6$)-alkyl)$_2$, CF$_3$, or two of the R11, R12, R13, R14, R15 and R16 groups together form a (C$_2$-C$_6$)-alkylene substituent which may be fused to a (C$_6$-C$_{10}$)-aryl group or a (C$_6$-C$_{10}$)-heterocycle group, and these aryl or heterocycle groups may be substituted by F, Cl, Br, I, OCF$_3$, CF$_3$, CN, (C$_1$-C$_6$)-alkyl, aryl, heterocycle, (C$_3$-C$_8$)-cycloalkyl, (C$_1$-C$_4$)-alkylene-O—(C$_1$-C$_6$)-alkyl, (C$_1$-C$_4$)-alkylene-S—(C$_1$-C$_6$)-alkyl, (C$_1$-C$_4$)-alkylene-NH—(C$_1$-C$_6$)-alkyl, (C$_1$-C$_4$)-alkylene-N((C$_1$-C$_6$)-alkyl)$_2$, (C$_1$-C$_4$)-alkylene-(C$_6$-C$_{10}$)-aryl, (C$_1$-C$_4$)-alkylene-heterocycle, COOH, COO(C$_1$-C$_6$)-alkyl, CONH$_2$, CONH(C$_1$-C$_6$)-alkyl, CON((C$_1$-C$_6$)-alkyl)$_2$, OH, O—(C$_1$-C$_6$)-alkyl, O—($C_3$-$C_6$)-cycloalkyl, S—($C_1$-$C_6$)-alkyl, S—($C_3$-$C_6$)-cycloalkyl, SO—($C_1$-$C_6$)-alkyl, SO—($C_3$-$C_6$)-cycloalkyl, $SO_2$—($C_1$-$C_6$)-alkyl, $SO_2$—($C_3$-$C_6$)-cycloalkyl, $SO_2$—$NH_2$, $SO_2$—NH—($C_1$-$C_6$)-alkyl or $SO_2$—NH—($C_3$-$C_7$)-cycloalkyl;

m is 0;

n is 0 or 1;

and the pharmaceutically acceptable salts thereof.

The present invention also comprises to compounds of formula I, in the form of their racemates, racemic mixtures, pure enantiomers, as well as their diastereomers and mixtures thereof.

When R-groups or substituents may occur more than once in the compounds of the formula I, they may all each independently have the definitions specified and be the same or different.

Owing to their higher water solubility, the pharmaceutically acceptable salts of the compounds of formula I of the present invention are particularly suitable for medical applications compared to the starting or base compounds. These salts must have a pharmaceutically acceptable anion or cation. Suitable pharmaceutically acceptable acid addition salts of the inventive compounds are salts of inorganic acids such as hydrochloric acid, hydrobromic acid, phosphoric acid, metaphosphoric acid, nitric acid and sulfuric acid, and organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1,3-propanediol), diethanolamine, lysine and ethylenediamine.

Salts with a pharmaceutically unacceptable anion, for example, trifluoroacetate, are also included within the scope of the invention as useful intermediates for the preparation or purification of pharmaceutically acceptable salts and/or for the use in non-therapeutic, for example in vitro, applications.

The term "physiologically functional derivative" used herein refers to any physiologically compatible derivative of an inventive compound of the formula I, for example an ester which, on administration to a mammal, for example the human, is capable (directly or indirectly) of forming a compound of the formula I or an active metabolite thereof.

The physiologically functional derivatives also include prodrugs of the inventive compounds. Such prodrugs are metabolized after administration to the patient in vivo resulting in the inventive compound which is then effective in therapeutically treating the disorder. These prodrugs may or may not themselves be active.

The inventive compounds may also be present in various polymorphic forms, for example as amorphous and crystalline polymorphic forms. All polymorphic forms of the inventive compounds are included within the scope of the invention and are a further aspect of the invention.

Hereinafter, all references to "compound(s) of formula (I)" relate to compound(s) of formula I as described above, and also their salts, solvates and physiologically functional derivatives as described herein.

An alkyl group means a straight-chain or branched hydrocarbon chain having one or more carbons, for example methyl, ethyl, isopropyl, tert-butyl and hexyl.

The alkyl groups may be mono- or poly-substituted by suitable groups, for example:

F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl, O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N(($C_1$-$C_6$)-alkyl)($CH_2$)$_n$-aryl, $SO_2$—N(($C_1$-$C_6$)-alkyl)($CH_2$)$_n$-heterocycle, $SO_2$—N(($CH_2$)$_n$-aryl)$_2$, $SO_2$—N(($CH_2$)$_n$-heterocycle)$_2$ wherein n may be 0-6 and the aryl or heterocyclic substituents may be di-substituted by F, Cl, Br, OH, $CF_3$, $NO_2$, CN, $OCF_3$, O—($C_1$-$C_6$)-alkyl, ($C_1$-$C_6$)-alkyl or $NH_2$;

C(=NH)($NH_2$), $NH_2$, NH—($C_1$-$C_6$)-alkyl, N(($C_1$-$C_6$)-alkyl)$_2$, NH($C_1$-$C_7$)-acyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N(($C_1$-$C_6$)-alkyl)-CO—($C_1$-$C_6$)-alkyl, N(($C_1$-$C_6$)-alkyl)-COO—($C_1$-$C_6$)-alkyl, N(($C_1$-$C_6$)-alkyl)-CO-aryl, N(($C_1$-$C_6$)-alkyl)-CO-heterocycle, N(($C_1$-$C_6$)-alkyl)-COO-aryl, N(($C_1$-$C_6$)-alkyl)-COO-heterocycle, N(($C_1$-$C_6$)-alkyl)-CO—NH—($C_1$-$C_6$)-alkyl), N(($C_1$-$C_6$)-alkyl)-CO—NH-aryl, N(($C_1$-$C_6$)-alkyl)-CO—NH-heterocycle, N(($C_1$-$C_6$)-alkyl)-CO—N(($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—($CH_2$)$_n$-aryl and O—($CH_2$)$_n$-heterocycle, wherein n may be 0-6, wherein the aryl substituent or heterocyclic group may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl or $CONH_2$.

An alkenyl group is a straight-chain or branched hydrocarbon chain having two or more carbons and one or more double bonds, for example vinyl, allyl, pentenyl, 2-methyl-but-2-en-4-yl.

The alkenyl substituents may be mono- or poly-substituted by suitable groups, for example:

F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl, O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—

$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N((C_1-C_6)$-alkyl)$(CH_2)_n$-aryl, $SO_2$—$N((C_1-C_6)$-alkyl)$(CH_2)_n$-heterocycle, $SO_2$—$N((CH_2)_n$-aryl)$_2$, $SO_2$—$N((CH_2)_n$-heterocycle)$_2$ wherein n may be 0-6 and the aryl radical or heterocyclic radical may be up to di-substituted by F, Cl, Br, OH, $CF_3$, $NO_2$, CN, $OCF_3$, O—$(C_1-C_6)$-alkyl, $(C_1-C_6)$-alkyl or $NH_2$;

$C(=NH)(NH_2)$, $NH_2$, NH—$(C_1-C_6)$-alkyl, $N((C_1-C_6)$-alkyl)$_2$, $NH(C_1-C_7)$-acyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, $N((C_1-C_6)$-alkyl)-CO—$(C_1-C_6)$-alkyl, $N((C_1-C_6)$-alkyl)-COO—$(C_1-C_6)$-alkyl, $N((C_1-C_6)$-alkyl)-CO-aryl, $N((C_1-C_6)$-alkyl)-CO-heterocycle, $N((C_1-C_6)$-alkyl)-COO-aryl, $N((C_1-C_6)$-alkyl)-COO-heterocycle, $N((C_1-C_6)$-alkyl)-CO—NH—$(C_1-C_6)$-alkyl), $N((C_1-C_6)$-alkyl)-CO—NH-aryl, $N((C_1-C_6)$-alkyl)-CO—NH-heterocycle, $N((C_1-C_6)$-alkyl)-CO—N$((C_1-C_6)$-alkyl)$_2$, $N((C_1-C_6)$-alkyl)-CO—$N((C_1-C_6)$-alkyl)-aryl, $N((C_1-C_6)$-alkyl)-CO—$N((C_1-C_6)$-alkyl)-heterocycle, $N((C_1-C_6)$-alkyl)-CO—N-(aryl)$_2$, $N((C_1-C_6)$-alkyl)-CO—N-(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl), N(aryl)-CO—NH-aryl, N(heterocycle)-CO—NH-aryl, N(aryl)-CO—$N((C_1-C_6)$-alkyl)$_2$, N(heterocycle)-CO—$N((C_1-C_6)$-alkyl)$_2$, N(aryl)-CO—$N((C_1-C_6)$-alkyl)-aryl, N(heterocycle)-CO—$N((C_1-C_6)$-alkyl)-aryl, N(aryl)-CO—N-(aryl)$_2$, N(heterocycle)-CO—N-(aryl)$_2$, aryl, O—$(CH_2)_n$-aryl and O—$(CH_2)_n$-heterocycle, wherein n may be 0-6, wherein the aryl radical or heterocyclic radical may be mono- to tri-substituted by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl)$_2$, $SO_2$—$CH_3$, COOH, COO—$(C_1-C_6)$-alkyl or $CONH_2$.

An alkynyl group is a straight-chain or branched hydrocarbon chain having two or more carbons and one or more triple bonds, for example ethynyl, propynyl, butynyl, hexynyl.

The alkynyl radicals may be mono- or poly-substituted by suitable groups, for example:

F, Cl, Br, I, $CF_3$, $NO_2$, $N_3$, CN, COOH, $COO(C_1-C_6)$alkyl, $CONH_2$, $CONH(C_1-C_6)$alkyl, $CON[(C_1-C_6)$alkyl]$_2$, cycloalkyl, $(C_2-C_6)$-alkenyl, $(C_2-C_6)$-alkynyl, O—$(C_1-C_6)$-alkyl, O—CO—$(C_1-C_6)$-alkyl, O—CO—$(C_1-C_6)$-aryl, O—CO—$(C_1-C_6)$-heterocycle;

$PO_3H_2$, $SO_3H$, $SO_2$—$NH_2$, $SO_2NH(C_1-C_6)$-alkyl, $SO_2N[(C_1-C_6)$-alkyl]$_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N((C_1-C_6)$-alkyl)$(CH_2)_n$-aryl, $SO_2$—$N((C_1-C_6)$-alkyl)$(CH_2)_n$-heterocycle, $SO_2$—$N((CH_2)_n$-aryl)$_2$, $SO_2$—$N((CH_2)_n$-heterocycle)$_2$ wherein n may be 0-6 and the aryl radical or heterocyclic radical may be up to di-substituted by F, Cl, Br, OH, $CF_3$, $NO_2$, CN, $OCF_3$, O—$(C_1-C_6)$-alkyl, $(C_1-C_6)$-alkyl or $NH_2$;

$C(=NH)(NH_2)$, $NH_2$, NH—$(C_1-C_6)$-alkyl, $N((C_1-C_6)$-alkyl)$_2$, $NH(C_1-C_7)$-acyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, $N((C_1-C_6)$-alkyl)-CO—$(C_1-C_6)$-alkyl, $N((C_1-C_6)$-alkyl)-COO—$(C_1-C_6)$-alkyl, $N((C_1-C_6)$-alkyl)-CO-aryl, $N((C_1-C_6)$-alkyl)-CO-heterocycle, $N((C_1-C_6)$-alkyl)-COO-aryl, $N((C_1-C_6)$-alkyl)-COO-heterocycle, $N((C_1-C_6)$-alkyl)-CO—NH—$(C_1-C_6)$-alkyl), $N((C_1-C_6)$-alkyl)-CO—NH-aryl, $N((C_1-C_6)$-alkyl)-CO—NH-heterocycle, $N((C_1-C_6)$-alkyl)-CO—N$((C_1-C_6)$-alkyl)$_2$, $N((C_1-C_6)$-alkyl)-CO—$N((C_1-C_6)$-alkyl)-aryl, $N((C_1-C_6)$-alkyl)-CO—$N((C_1-C_6)$-alkyl)-heterocycle, $N((C_1-C_6)$-alkyl)-CO—N-(aryl)$_2$, $N((C_1-C_6)$-alkyl)-CO—N-(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl), N(aryl)-CO—NH-aryl, N(heterocycle)-CO—NH-aryl, N(aryl)-CO—$N((C_1-C_6)$-alkyl)$_2$, N(heterocycle)-CO—$N((C_1-C_6)$-alkyl)$_2$, N(aryl)-CO—$N((C_1-C_6)$-alkyl)-aryl, N(heterocycle)-CO—$N((C_1-C_6)$-alkyl)-aryl, N(aryl)-CO—N-(aryl)$_2$, N(heterocycle)-CO—N-(aryl)$_2$, aryl, O—$(CH_2)_n$-aryl and O—$(CH_2)_n$-heterocycle, wherein n may be 0-6, wherein the aryl radical or heterocyclic radical may be mono- to trisubstituted by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl)$_2$, $SO_2$—$CH_3$, COOH, COO—$(C_1-C_6)$-alkyl or $CONH_2$.

An aryl group is a phenyl, naphthyl, biphenyl, tetra-hydronaphthyl, alpha- or beta-tetralonyl, indanyl or indan-1-onyl radical.

The aryl radicals may be mono- or poly-substituted by suitable groups, for example:

F, Cl, Br, I, $CF_3$, $NO_2$, $N_3$, CN, COOH, $COO(C_1-C_6)$alkyl, $CONH_2$, $CONH(C_1-C_6)$alkyl, $CON[(C_1-C_6)$alkyl]$_2$, cycloalkyl, $(C_2-C_6)$-alkenyl, $(C_2-C_6)$-alkynyl, O—$(C_1-C_6)$-alkyl, O—CO—$(C_1-C_6)$-alkyl, O—CO—$(C_1-C_6)$-aryl, O—CO—$(C_1-C_6)$-heterocycle;

$PO_3H_2$, $SO_3H$, $SO_2$—$NH_2$, $SO_2NH(C_1-C_6)$-alkyl, $SO_2N[(C_1-C_6)$-alkyl]$_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N((C_1-C_6)$-alkyl)$(CH_2)_n$-aryl, $SO_2$—$N((C_1-C_6)$-alkyl)$(CH_2)_n$-heterocycle, $SO_2$—$N((CH_2)_n$-aryl)$_2$, $SO_2$—$N((CH_2)_n$-heterocycle)$_2$ wherein n may be 0-6 and the aryl radical or heterocyclic radical may be up to di-substituted by F, Cl, Br, OH, $CF_3$, $NO_2$, CN, $OCF_3$, O—$(C_1-C_6)$-alkyl, $(C_1-C_6)$-alkyl or $NH_2$;

$C(=NH)(NH_2)$, $NH_2$, NH—$(C_1-C_6)$-alkyl, $N((C_1-C_6)$-alkyl)$_2$, $NH(C_1-C_7)$-acyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, $N((C_1-C_6)$-alkyl)-CO—$(C_1-C_6)$-alkyl, $N((C_1-C_6)$-alkyl)-COO—$(C_1-C_6)$-alkyl, $N((C_1-C_6)$-alkyl)-CO-aryl, $N((C_1-C_6)$-alkyl)-CO-heterocycle, $N((C_1-C_6)$-alkyl)-COO-aryl, $N((C_1-C_6)$-alkyl)-COO-heterocycle, $N((C_1-C_6)$-alkyl)-CO—NH—$(C_1-C_6)$-alkyl), $N((C_1-C_6)$-alkyl)-CO—NH-aryl, $N((C_1-C_6)$-alkyl)-CO—NH-heterocycle, $N((C_1-C_6)$-alkyl)-CO—N$((C_1-C_6)$-alkyl)$_2$, $N((C_1-C_6)$-alkyl)-CO—$N((C_1-C_6)$-alkyl)-aryl, $N((C_1-C_6)$-alkyl)-CO—$N((C_1-C_6)$-alkyl)-heterocycle, $N((C_1-C_6)$-alkyl)-CO—N-(aryl)$_2$, $N((C_1-C_6)$-alkyl)-CO—N-(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl), N(heterocycle)-CO—NH—$(C_1-C_6)$-alkyl), N(aryl)-CO—NH-aryl, N(heterocycle)-CO—NH-aryl, N(aryl)-CO—$N((C_1-C_6)$- alkyl)$_2$, N(heterocycle)-CO—N((C$_1$-C$_6$)-alkyl)$_2$, N(aryl)-CO—N((C$_1$-C$_6$)-alkyl)-aryl, N(heterocycle)-CO—N((C$_1$-C$_6$)-alkyl)-aryl, N(aryl)-CO—N-(aryl)$_2$, N(heterocycle)-CO—N-(aryl)$_2$, aryl, O—(CH$_2$)$_n$-aryl and O—(CH$_2$)$_n$-heterocycle, wherein n may be 0-6, wherein the aryl radical or heterocyclic radical may be mono- to tri-substituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$.

A cycloalkyl radical is understood to mean a ring system which comprises one or more rings and is present in saturated or partially unsaturated form (with one or two double bonds), and is formed exclusively from carbon atoms, for example cyclopropyl, cyclopentyl, cyclopentenyl, cyclohexyl or adamantyl.

The cycloalkyl radicals may be mono- or poly-substituted by suitable groups, for example:

F, Cl, Br, I, CF$_3$, NO$_2$, N$_3$, CN, COOH, COO(C$_1$-C$_6$)alkyl, CONH$_2$, CONH(C$_1$-C$_6$)alkyl, CON[(C$_1$-C$_6$)alkyl]$_2$, cycloalkyl, (C$_2$-C$_6$)-alkenyl, (C$_2$-C$_6$)-alkynyl, O—(C$_1$-C$_6$)-alkyl, O—CO—(C$_1$-C$_6$)-alkyl, O—CO—(C$_1$-C$_6$)-aryl, O—CO—(C$_1$-C$_6$)-heterocycle;

PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N((C$_1$-C$_6$)-alkyl)(CH$_2$)$_n$-aryl, SO$_2$—N((C$_1$-C$_6$)-alkyl)(CH$_2$)$_n$-heterocycle, SO$_2$—N((CH$_2$)$_n$-aryl)$_2$, SO$_2$—N((CH$_2$)$_n$-heterocycle)$_2$ wherein n may be 0-6 and the aryl radical or heterocyclic radical may be up to disubstituted by F, Cl, Br, OH, CF$_3$, NO$_2$, CN, OCF$_3$, O—(C$_1$-C$_6$)-alkyl, (C$_1$-C$_6$)-alkyl or NH$_2$;

C(=NH)(NH$_2$), NH$_2$, NH—(C$_1$-C$_6$)-alkyl, N((C$_1$-C$_6$)-alkyl)$_2$, NH(C$_1$-C$_7$)-acyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N((C$_1$-C$_6$)-alkyl)-CO—(C$_1$-C$_6$)-alkyl, N((C$_1$-C$_6$)-alkyl)-COO—(C$_1$-C$_6$)-alkyl, N((C$_1$-C$_6$)-alkyl)-CO-aryl, N((C$_1$-C$_6$)-alkyl)-CO-heterocycle, N((C$_1$-C$_6$)-alkyl)-COO-aryl, N((C$_1$-C$_6$)-alkyl)-COO-heterocycle, N((C$_1$-C$_6$)-alkyl)-CO—NH—(C$_1$-C$_6$)-alkyl), N((C$_1$-C$_6$)-alkyl)-CO—NH-aryl, N((C$_1$-C$_6$)-alkyl)-CO—NH-heterocycle, N((C$_1$-C$_6$)-alkyl)-CO—N((C$_1$-C$_6$)-alkyl)$_2$, N((C$_1$-C$_6$)-alkyl)-CO—N((C$_1$-C$_6$)-alkyl)-aryl, N((C$_1$-C$_6$)-alkyl)-CO—N((C$_1$-C$_6$)-alkyl)-heterocycle, N((C$_1$-C$_6$)-alkyl)-CO—N-(aryl)$_2$, N((C$_1$-C$_6$)-alkyl)-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl), N(aryl)-CO—NH-aryl, N(heterocycle)-CO—NH-aryl, N(aryl)-CO—N((C$_1$-C$_6$)-alkyl)$_2$, N(heterocycle)-CO—N((C$_1$-C$_6$)-alkyl)$_2$, N(aryl)-CO—N((C$_1$-C$_6$)-alkyl)-aryl, N(heterocycle)-CO—N((C$_1$-C$_6$)-alkyl)-aryl, N(aryl)-CO—N-(aryl)$_2$, N(heterocycle)-CO—N-(aryl)$_2$, aryl, O—(CH$_2$)$_n$-aryl and O—(CH$_2$)$_n$-heterocycle, wherein n may be 0-6, wherein the aryl radical or heterocyclic radical may be mono- to tri-substituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, COOH, COO—(C$_1$-C$_6$)-alkyl or CONH$_2$.

Heterocycle, heterocycle and heterocyclic substituents are rings and ring systems which, apart from carbon, also contain heteroatoms, for example nitrogen, oxygen or sulfur. This definition also includes ring systems in which the heterocycle or the heterocyclic group is fused to one or more benzene rings. The heterocycle or the heterocyclic group may be aromatic, saturated aliphatic or partially unsaturated aliphatic.

Suitable heterocycle substituents or "heterocyclic groups" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl is 2-, 3- or 4-pyridyl. Thienyl is 2- or 3-thienyl. Furyl is 2- or 3-furyl.

Also included are the corresponding N-oxides of these compounds, i.e., for example, 1-oxy-2-, -3- or -4-pyridyl.

Also included are mono- or poly-benzofused derivatives of these heterocycles.

The heterocyclic rings or heterocyclic substituents may be mono- or poly-substituted by suitable groups, for example: F, Cl, Br, I, CF$_3$, NO$_2$, N$_3$, CN, COOH, COO(C$_1$-C$_6$)alkyl, CONH$_2$, CONH(C$_1$-C$_6$)alkyl, CON[(C$_1$-C$_6$)alkyl]$_2$, cycloalkyl, (C$_2$-C$_6$)-alkenyl, (C$_2$-C$_6$)-alkynyl, O—(C$_1$-C$_6$)-alkyl, O—CO—(C$_1$-C$_6$)-alkyl, O—CO—(C$_1$-C$_6$)-aryl, O—CO—(C$_1$-C$_6$)-heterocycle;

PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N((C$_1$-C$_6$)-alkyl)(CH$_2$)$_n$-aryl, SO$_2$—N((C$_1$-C$_6$)-alkyl)(CH$_2$)$_n$-heterocycle, SO$_2$—N((CH$_2$)$_n$-aryl)$_2$, SO$_2$—N((CH$_2$)$_n$-heterocycle)$_2$ wherein n may be 0-6 and the aryl radical or heterocyclic radical may be up to disubstituted by F, Cl, Br, OH, CF$_3$, NO$_2$, CN, OCF$_3$, O—(C$_1$-C$_6$)-alkyl, (C$_1$-C$_6$)-alkyl or NH$_2$;

C(=NH)(NH$_2$), NH$_2$, NH—(C$_1$-C$_6$)-alkyl, N((C$_1$-C$_6$)-alkyl)$_2$, NH(C$_1$-C$_7$)-acyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N((C$_1$-C$_6$)-alkyl)-CO—(C$_1$-C$_6$)-alkyl, N((C$_1$-C$_6$)-alkyl)-COO—(C$_1$-C$_6$)-alkyl, N((C$_1$-C$_6$)-alkyl)-CO-aryl, N((C$_1$-C$_6$)-alkyl)-CO-heterocycle, N((C$_1$-C$_6$)-alkyl)-COO-aryl, N((C$_1$-C$_6$)-alkyl)-COO-heterocycle, N((C$_1$-C$_6$)-alkyl)-CO—NH—(C$_1$-C$_6$)-alkyl), N((C$_1$-C$_6$)-alkyl)-CO—NH-aryl, N((C$_1$-C$_6$)-alkyl)-CO—NH-heterocycle, N((C$_1$-C$_6$)-alkyl)-CO—N((C$_1$-C$_6$)-alkyl)$_2$, N((C$_1$-C$_6$)-alkyl)-CO—N((C$_1$-C$_6$)-alkyl)- aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N(($C_1$-$C_6$)-alkyl)$_2$, N(heterocycle)-CO—N(($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—(CH$_2$)$_n$-aryl and O—(CH$_2$)$_n$-heterocycle, wherein n may be 0-6, wherein the aryl radical or heterocyclic radical may be mono- to trisubstituted by F, Cl, Br, I, OH, CF$_3$, NO$_2$, CN, OCF$_3$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, COOH, COO—($C_1$-$C_6$)-alkyl or CONH$_2$.

The compound(s) of the present invention as defined by formula (I) may also be administered in combination with additional active ingredients.

The amount of a compound of formula I which is required in order to achieve the desired biological effect is dependent upon a series of factors, for example the specific compound selected, the intended use, the mode of administration and the clinical condition of the patient. The daily dose is generally in the range from 0.3 mg to 100 mg (typically from 3 mg to 50 mg) per day per kilogram of bodyweight, for example 3-10 mg/kg/day. An intravenous dose may, for example, be in the range from 0.3 mg to 1.0 mg/kg and may suitably be administered as an infusion of from 10 ng to 100 ng per kilogram per minute. Suitable infusion solutions for these purposes may, for example, contain from 0.1 ng to 10 mg, typically from 1 ng to 10 ng, per milliliter. Single doses may contain, for example, from 1 mg to 10 g of the active ingredient. Ampoules for injections may therefore contain, for example, from 1 mg to 100 mg, and single dose formulations which can be administered orally, for example tablets or capsules, may contain, for example, from 1.0 to 1000 mg, typically from 10 to 600 mg. The compounds of the formula I may be used for therapy of the abovementioned conditions as the compounds themselves, although they are preferably in the form of a pharmaceutical composition with an acceptable carrier. The carrier of course has to be acceptable, in the sense that it is compatible with the other constituents of the composition and is not damaging to the health of the patient. The carrier may be a solid or a liquid or both and is preferably formulated with the compound as a single dose, for example as a tablet, which may contain from 0.05 to 95% by weight of the active ingredient. Further pharmaceutically active substances may likewise be present, including further compounds of the formula I. The inventive pharmaceutical compositions may be produced by one of the known pharmaceutical methods which consist essentially in mixing the constituents with pharmacologically acceptable carriers, inert bulking agents and/or excipients.

Inventive pharmaceutical compositions are those which are suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the type of the compound of the formula I used in each case. Coated formulations and coated slow-release formulations are also encompassed by the scope of the invention. Preference is given to acid- and gastric fluid-resistant formulations. Suitable gastric fluid-resistant coatings include cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units, for example capsules, cachets, lozenges or tablets, each of which contains a certain amount of the compound of the formula I; as powder or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional constituents) are brought into contact. In general, the compositions are prepared by uniform and homogeneous mixing of the active ingredient with a liquid carrier and/or finely divided solid carrier, after which the product is shaped if necessary. For example, a tablet can thus be produced by compressing or shaping a powder or granules of the compound, optionally with one or more additional constituents. Compressed tablets can be prepared by tableting the compound in free-flowing form, for example a powder or granules, optionally mixed with a binder, lubricant, inert diluent and/or one (or more) surfactants/dispersants in a suitable machine. Shaped tablets can be prepared by shaping the pulverulent compound moistened with an inert liquid diluent in a suitable machine.

Pharmaceutical compositions which are suitable for peroral (sublingual) administration include lozenges which contain a compound of the formula I with a flavoring, customarily sucrose, and gum arabic or tragacanth, and pastilles which include the compound in an inert base, such as gelatin and glycerol or sucrose and gum arabic.

Suitable pharmaceutical compositions for parenteral administration include preferably sterile aqueous preparations of a compound of the formula I which are preferably isotonic with the blood of the intended recipient. These preparations are preferably administered intravenously, although the administration may also be subcutaneous, intramuscular or intradermal as an injection. These preparations can preferably be produced by mixing the compound with water and making the solution obtained sterile and isotonic with the blood. Injectable compositions according to the invention generally contain from 0.1 to 5% by weight of the active compound.

Suitable pharmaceutical compositions for rectal administration are preferably in the form of single dose suppositories. These can be prepared by mixing a compound of the formula I with one or more conventional solid carriers, for example cocoa butter, and shaping the resulting mixture.

Suitable pharmaceutical compositions for topical application on the skin are preferably in the form of an ointment, cream, lotion, paste, spray, aerosol or oil. Useful carriers include petroleum jelly, lanolin, polyethylene glycols, alcohols and combinations of two or more of these substances. The active ingredient is generally present in a concentration of from 0.1 to 15% by weight of the composition, for example from 0.5 to 2%.

Transdermal administration is also a route of possible administration. Suitable pharmaceutical compositions for transdermal applications may be in the form of single plasters which are suitable for long-term close contact with the epidermis of the patient. Such plasters suitably contain the active ingredient in an optionally buffered aqueous solution, dissolved and/or dispersed in an adhesive or dispersed in a polymer. A suitable active ingredient concentration is from approx. 1% to 35%, preferably from approx. 3% to 15%. A particular means of releasing the active ingredient may be by electrotransport or iontophoresis, as described, for example, in Pharmaceutical Research, 2(6): 318 (1986) which is hereby incorporated by reference herein.

Further useful active ingredients for combination products are as follows:

All anti-diabetics mentioned in the Rote Liste 2005, chapter 12 which is hereby incorporated herein by reference. They can be combined with the inventive compounds of the formula I, in particular for synergistic enhancement of action. The active ingredient combination can be administered either by separately administering the active ingredients to the patient or in the form of combination products in which a plurality of active ingredients are present in one pharmaceutical preparation. Most of the active ingredients listed hereinbelow are disclosed in USP Dictionary of USAN and International Drug Names, US Pharmacopeia, Rockville 2001.

Anti-diabetics include insulin and insulin derivatives, for example Lantus® (see www.lantus.com) or HMR 1964, fast-acting insulins (see U.S. Pat. No. 6,221,633 to Ertl et. al.), GLP-1 derivatives, for example those disclosed in WO 98/08871 of Novo Nordisk A/S which are hereby incorporated by reference herein, and other orally active hypoglycemic active ingredients.

The orally active hypoglycemic active ingredients preferably include sulfonylureas, biguanidines, meglitinides, oxadiazolidinediones, thiazolidinediones, glucosidase inhibitors, glucagon antagonists, GLP-1 agonists, potassium channel openers, for example those disclosed in WO 97/26265 and WO 99/03861 of Novo Nordisk A/S, insulin sensitizers, inhibitors of liver enzymes which are involved in the stimulation of gluconeogenesis and/or glycogenolysis, modulators of glucose uptake, compounds which alter lipid metabolism such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMG-CoA reductase inhibitor such as simvastatin, fluvastatin, pravastatin, lovastatin, atorvastatin, cerivastatin or rosuvastatin.

In one embodiment of the invention, the compounds of the formula I are administered in combination with a cholesterol absorption inhibitor, for example, ezetimibe, tiqueside, pamaqueside, or with a compound as described in PCT/EP 2004/00269, PCT/EP 2003/05815, PCT/EP 2003/05814, PCT/EP 2003/05816, EP 0114531 or U.S. Pat. No. 6,498,156 to Glombek et. al.

In one embodiment of the invention, the compounds of the formula I are administered in combination with a PPAR gamma agonist, for example, rosiglitazone, pioglitazone, JTT-501 or GI 262570.

In one embodiment of the invention, the compounds of the formula I are administered in combination with PPAR alpha agonist, for example, GW 9578, GW 7647.

In one embodiment of the invention, the compounds of the formula I are administered in combination with a mixed PPAR alpha/gamma agonist, for example, GW 1536, AVE 8042, AVE 8134, AVE 0847, or as described in PCT/US 11833, PCT/US 11490, DE10142734.4. which are hereby incorporated by reference herein.

In one embodiment of the invention, the compounds of the formula I are administered in combination with a fibrate, for example fenofibrate, clofibrate or bezafibrate.

In one embodiment of the invention, the compounds of the formula I are administered in combination with an MTP inhibitor, for example implitapide, BMS-201038 or R-103757.

In one embodiment of the invention, the compounds of the formula I are administered in combination with a bile acid absorption inhibitor (see, for example, U.S. Pat. No. 6,245,744 or 6,221,897, both to Frick et. al.).

In one embodiment of the invention, the compounds of the formula I are administered in combination with a CETP inhibitor, for example JTT-705.

In one embodiment of the invention, the compounds of the formula I are administered in combination with a polymeric bile acid adsorber, for example cholestyramine or colesevelam.

In one embodiment of the invention, the compounds of the formula I are administered in combination with an LDL receptor inducer (see U.S. Pat. No. 6,342,512 to Kirsch et. al.).

In one embodiment of the invention, the compounds of the formula I are administered in combination with an ACAT inhibitor, for example avasimibe.

In one embodiment of the invention, the compounds of the formula I are administered in combination with an antioxidant, for example OPC-14117.

In one embodiment of the invention, the compounds of the formula I are administered in combination with a lipoprotein lipase inhibitor, for example NO-1886.

In one embodiment of the invention, the compounds of the formula I are administered in combination with an ATP citrate lyase inhibitor, for example SB-204990.

In one embodiment of the invention, the compounds of the formula I are administered in combination with a squalene synthetase inhibitor, for example BMS-188494.

In one embodiment of the invention, the compounds of the formula I are administered in combination with a lipoprotein (a) antagonist, for example CI-1027 or nicotinic acid.

In one embodiment of the invention, the compounds of the formula I are administered in combination with a lipase inhibitor, for example orlistat.

In one embodiment of the invention, the compounds of the formula I are administered in combination with insulin.

In one embodiment, the compounds of the formula I are administered in combination with a sulfonylurea, for example tolbutamide, glibenclamide, glipizide or glimepiride.

In one embodiment, the compounds of the formula I are administered in combination with a biguanide, for example metformin.

In one embodiment, the compounds of the formula I are administered in combination with a meglitinide, for example repaglinide.

In one embodiment, the compounds of the formula I are administered in combination with a thiazolidinedione, for example troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]-phenyl]methyl]-2,4-thiazolidinedione.

In one embodiment, the compounds of the formula I are administered in combination with an α-glucosidase inhibitor, for example miglitol or acarbose.

In one embodiment, the compounds of the formula I are administered in combination with adenosine A1 agonists, for example those which are described in EP 0912520 or PCT/EP06749 which are hereby incorporated by reference herein.

In one embodiment, the compounds of the formula I are administered in combination with an active ingredient which acts on the ATP-dependent potassium channel of the beta cells, for example tolbutamide, glibenclamide, glipizide, glimepiride or repaglinide.

In one embodiment, the compounds of the formula I are administered in combination with more than one of the above-mentioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)-methyl] cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxo-ethyl]amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), CB1 (cannabinoid receptor 1) receptor antagonists (e.g. rimonabant or the active ingredients specified in WO 02/28346), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethyl-carbamoyl)-3,4-dihydro-1H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine or doprexin), lipase/amylase inhibitors (see, for example, WO 00/40569), PPAR modulators (see, for example, WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphatamine or amphetamine.

In another embodiment, the other active ingredient is fenfluramine or dexfenfluramine.

In another embodiment, the other active ingredient is sibutramine.

In another embodiment, the other active ingredient is orlistat.

In another embodiment, the other active ingredient is mazindol or phentermine.

In another embodiment, the other active ingredient is rimonabant.

In one embodiment, the compounds of the formula I are administered in combination with dietary fiber materials, preferably insoluble dietary fiber materials (see, for example, Carob/Caromax® (Zunft H J; et al., Carob pulp preparation for treatment of hypercholesterolemia, ADVANCES IN THERAPY (2001 September-October), 18(5), 230-6.) Caromax is a carob-containing product supplied by Nutrinova, Nutrition Specialties & Food Ingredients GmbH, Industriepark Höchst, 65926 Frankfurt/Main). Combination with Caromax® is possible in one preparation or by separate administration of compounds of the formula I and Caromax®. Caromax® can also be administered in the form of foodstuffs, for example, in bakery products or muesli bars.

Notwithstanding their teachings and their relative pertenance to the present invention at hand, all of the afore-described references are hereby incorporated by reference herein. It will be furthermore be appreciated that any suitable combination of the compounds according to the invention with one or more of the above-mentioned compounds and optionally one or more further pharmacologically active substances is regarded as being covered by the scope of protection of the present invention. Moreover, the tabulated examples listed below are provided to better illustrate methods for practicing the present invention as disclosed herein. The examples are provided to better describe and more specifically set forth the compounds, processes and methods of the present invention as contemplated herein. However, it is to be recognized that they are for illustrative purposes only, and should not be interpreted as limiting the spirit and scope of the invention as later recited by the claims that follow.

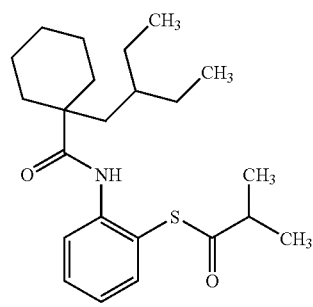

JTT-705

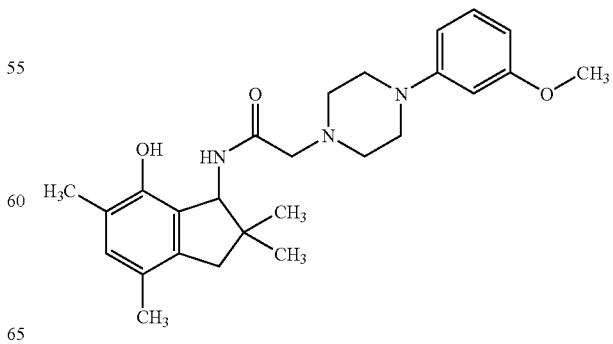

OPC-14117

SB-204990

NO-1886

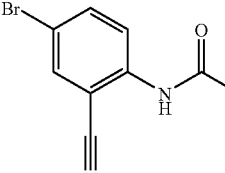

CI-1027

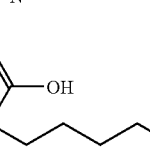

BMS-188494

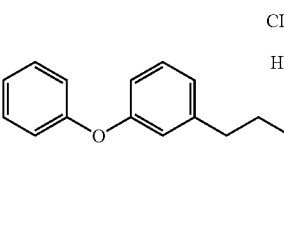

GI 262570

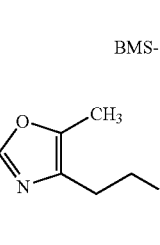

JTT-501

The compounds of the formula I can be prepared by reacting suitable starting materials of the formula II in which R1, R2 and R3 are each as defined above and X is a leaving group, such as chlorine, bromine, iodine, sulfonyl oxide, sulfinyl or sulfoxyl, with a compound of the formula V, optionally in the presence of suitable bases, to give the compounds of the formula IV.

Alternatively, compounds of the formula III in which R1, R2 and R3 are each as defined above are reacted with alkylating agents of the formula VI to give the compounds of the formula IV, wherein X is a suitable leaving group, for example chlorine, bromine, iodine, sulfonyloxy, sulfinyl or sulfoxyl.

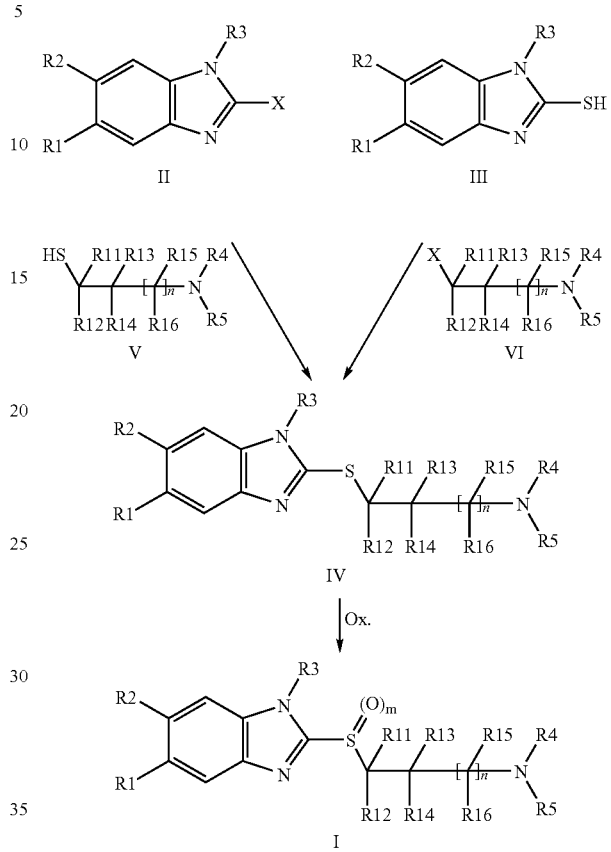

In the cases wherein $R^4$ or $R^5$ is hydrogen, it may be appropriate to use the $-NR^4R^5$ radical in a form protected on the nitrogen function and to detach the protecting group again at a suitable point in the reaction. Such suitable protecting groups and the processes for their introduction and detachment are known (see: Theodora W. Greene and Peter G. M. Wuts, Protective Groups in Organic Synthesis, 3rd Edition, John Wiley & Sons, Inc., New York, 1999).

The thioether function in IV can then be oxidized by known methods to the inventive substances of the formula I in which n is 1 or 2.

The halogen compounds of the formula II can be obtained by known processes, for example by halogenating the corresponding H compound (formula II, X=H). Suitable halogenating agents may, by way of example, be halogens such as chlorine and bromine, N-bromosuccinimide, phosphorus pentoxide or phosphorus oxychloride. The synthesis of compounds of the formula II is described in the literature. They can, for example, be prepared by condensing substituted diaminobenzene derivatives with aldehydes in the presence of an oxidizing agent (for example atmospheric oxygen, oxygen, iodine, oxone, quinones, peroxides, etc.) or alternatively with carboxylic acids, nitriles or amides, without or in the presence of a catalyst.

Once again the examples provided below are done so to illustrate how to better practice the specific modes of the present inventive compounds and should not be interpreted or construed as limiting the spirit and scope of the invention as later recited by the claims that follow.

TABLE 1

| Ex. | R1 | R2 | R3 | m | R4 | R5 | R11 | R12 | R13 | R14 | n | R15 | R16 |
|-----|----|----|----|---|----|----|-----|-----|-----|-----|---|-----|-----|
| 1 | H | Ph-CO—NH— | —CH$_2$CH═C(CH$_3$)$_2$ | 0 | H | (TFA salt) | H | H | H | H | 1 | H | H |
| 2 | H | Ph-CH$_2$—NH— | —CH$_2$CH═C(CH$_3$)$_2$ | 0 | H | (TFA salt) | H | H | H | H | 1 | H | H |
| 3 | H | Ph-CO—NH— | —CH$_2$CH═C(CH$_3$)$_2$ | 0 | H | (TFA salt) | H | H | H | H | 0 | — | — |

The compounds of the formula I are notable for favorable effects on lipid and carbohydrate metabolism; in particular, they lower the blood sugar level and are suitable for the treatment of type II diabetes, of insulin resistance, of dyslipidemias and of metabolic syndrome/syndrome X. Moreover, the compounds are suitable for the treatment and prophylaxis of arteriosclerotic manifestations. The compounds can be used alone or in combination with further blood sugar-lowering active ingredients. The compounds act as DPP IV (dipeptidyl peptidase IV) inhibitors and are also suitable for the treatment of disorders of perception and other psychiatric indications, for example depressions, anxiety states, anxiety neuroses, schizophrenia, and for the treatment of disorders associated with the circadian rhythm, for weight reduction in mammals, for the treatment of immune disorders and for the treatment of drug abuse.

They are additionally suitable for the treatment of cancer, arthritis, osteoarthritis, osteoporosis, sleep disorders, sleep apnea, masculine and feminine sexual disorders, inflammations, acne, pigmentation of the skin, disorders of steroid metabolism, skin diseases, psoriasis, mycoses, neurodegenerative disorders, multiple sclerosis and Alzheimer's disease.

The efficacy of the compounds was tested as follows:

Measurement of the DPP-IV Activity:

Material:

DPP-IV from porcine kidneys (Sigma, Munich)

H-Ala-Pro-AFC (Bachem, Weil am Rhein)

Test Conditions:

DPP-IV (1 mU/ml, end concentration)

H-Ala-Pro-AFC (15 µm end concentration)

in Tris/HCl (40 mM, pH 7.4), total volume 0.2 ml

The reaction was performed at room temperature for different periods (typically 10 minutes) and stopped at the end of the reaction by adding 20 µl of ZnCl$_2$ (1 M). The conversion of H-Ala-Pro-AFC was determined fluorimetrically by measuring the emission at 535 nm on excitation at 405 nm. In the case of addition of inhibitors, the buffer volume added was adjusted such that a total volume of the test mixture of 200 µl was maintained.

% inhibition at a fixed concentration was calculated as follows:

$$(1 - \text{enzyme activity}_{inhibited\ reaction}/\text{enzyme activity}_{uninhibited\ reaction}) \times 100$$

TABLE 2

| Biological activity | |
|---|---|
| Working Example No. | % inhibition at 30 µM |
| 2 | 8 |
| 3 | 20 |

It can be seen from the tables that the compounds of the formula I inhibit the activity of the DPP-IV (dipeptidyl peptidase IV) and are thus suitable for lowering the blood sugar level.

The preparation of some examples will be described in detail hereinafter; the other examples were obtained analogously:

Example 1

N-[2-(3-Aminopropylsulfanyl)-1-(3-methylbut-2-enyl)-1H-benzimidazol-6-yl]benzamide trifluoroacetic acid salt a) tert-Butyl [3-(5/6-nitro-1H-benzimidazol-2-ylsulfanyl)propyl]carbamate

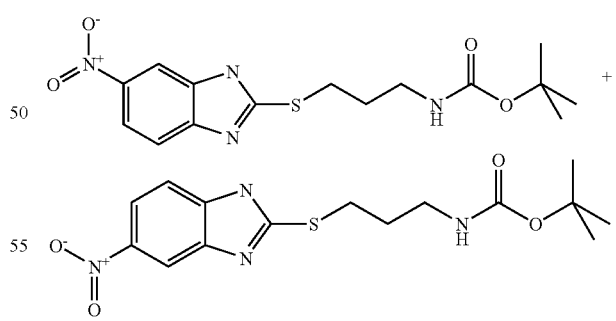

A solution of 1.0 g (5.12 mmol) of 5-nitrobenzimidazole-2-thiol and 790 µl (5.63 mmol) of triethylamine in 40 ml of tetrahydrofuran was stirred for 10 minutes and then admixed with a solution of tert-butyl 3-(bromopropyl)carbamate in 10 ml of tetrahydrofuran. The mixture was heated to 70° C. and stirred for 72 hours. The reaction mixture was concentrated under reduced pressure and separated by means of preparative HPLC (acetonitrile/water+0.5% trifluoroacetic acid, gradient: 20/80 to 100/0). 180 mg (18%) of reactant and 1.17 g (65%) of the desired product were obtained.

MS: m/z=353 (M+H)⁺.

b) tert-Butyl {3-[1-(3-methylbut-2-enyl)-5-nitro-1H-benzimidazol-2-ylsulfanyl]propyl}carbamate

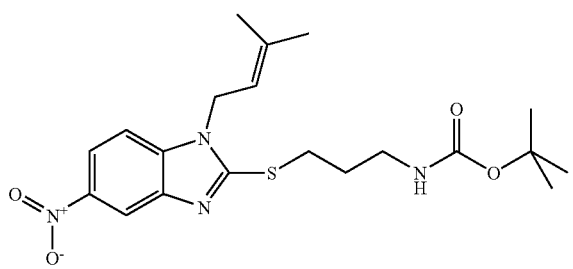

1.60 g (4.90 mmol) of cesium carbonate were added to a solution of 1.15 g (3.26 mmol) of tert-butyl [3-(5/6-nitro-1H-benzimidazol-2-ylsulfanyl)propyl]carbamate in 20 ml of dimethylformamide, and the mixture was stirred at room temperature for 30 minutes. Subsequently, 535 mg (3.59 mmol) of 1-bromo-3-methyl-2-butene were slowly added dropwise. The reaction mixture was concentrated under reduced pressure and partitioned between water and dichloromethane. The organic phase was dried and concentrated under reduced pressure. The crude mixture was separated on silica gel (heptane/ethyl acetate, gradient: 90:10 to 0:100). 145 mg (11%) of the desired product, 426 mg (31%) of a mixed fraction and 406 mg (30%) of tert-butyl {3-[1-(3-methylbut-2-enyl)-5-nitro-1H-benzimidazol-2-ylsulfanyl]propyl}carbamate were obtained.

MS: m/z=421 (M+H)⁺.

c) tert-Butyl {3-[6-amino-1-(3-methylbut-2-enyl)-1H-benzimidazol-2-ylsulfanyl]propyl}carbamate

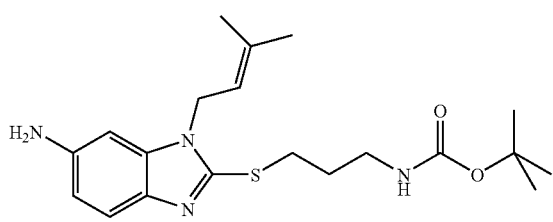

A solution of 140 mg (0.33 mmol) of tert-butyl {3-[1-(3-methylbut-2-enyl)-6-nitro-1H-benzimidazol-2-ylsulfanyl]propyl}carbamate in 15 ml of ethanol was added dropwise to a suspension of 93 mg (1.66 mmol) of iron and 16 mg (0.30 mmol) of ammonium chloride in 1.5 ml of water and boiled at reflux for 3 hours. The catalyst was filtered off and washed with ethanol. The filtrate was concentrated under reduced pressure. The 138 mg of the desired product thus obtained were used in the next stage without further purification.

d) tert-Butyl {3-[6-benzoylamino-1-(3-methylbut-2-enyl)-1H-benzimidazol-2-ylsulfanyl]propyl}carbamate

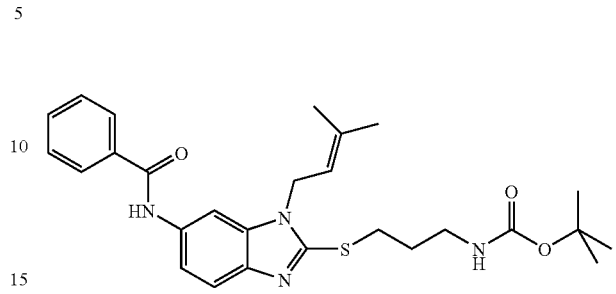

24 mg (0.07 mmol) of cesium carbonate were added to a solution of 58 mg of tert-butyl {3-[6-amino-1-(3-methylbut-2-enyl)-1H-benzimidazol-2-ylsulfanyl]propyl}carbamate (obtained analogously to examples 1a-c) in 5 ml of dimethylformamide, and the mixture was stirred at room temperature for 30 minutes. Subsequently, 17 μl (0.15 mmol) of benzoyl bromide were added and the mixture was stirred at room temperature for 20 hours. The reaction mixture was concentrated under reduced pressure and partitioned between water and dichloromethane. The organic phase was dried, concentrated under reduced pressure and purified by means of preparative HPLC (acetonitrile/water+0.5% trifluoroacetic acid, gradient: 20/80 to 100/0). 33 mg (44%) of the desired product were obtained.

MS: m/z=495 (M+H)⁺.

e) N-[2-(3-Aminopropylsulfanyl)-1-(3-methylbut-2-enyl)-1H-benzimidazol-6-yl]benzamide trifluoroacetic acid salt (A003423930A)

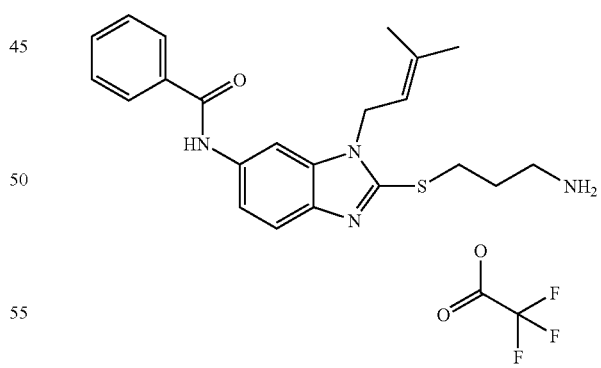

33 mg (0.07 mmol) of tert-butyl {3-[6-benzoylamino-1-(3-methylbut-2-enyl)-1H-benzimidazol-2-ylsulfanyl]propyl}carbamate were dissolved in 102 μl of trifluoroacetic acid and 100 μl of water and stirred at room temperature for 6 hours. The reaction mixture was diluted with water and freeze-dried. 34 mg of the desired product were obtained in quantitative yield.

MS: m/z=509 (M+H)⁺.

What is claimed is:

1. The compound of formula I

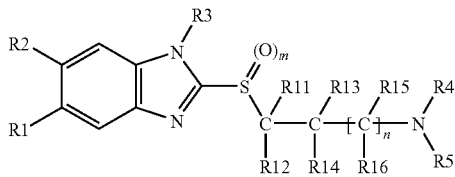

wherein
R1 is H;
R2 is NR24R25;
R24 is $(C_1-C_6)$-alkylene-$(C_6-C_{10})$-aryl wherein the aryl substituent may be mono- or poly-substituted by F, Cl, Br, I, CN, $NO_2$, SH, OH, $(C_1-C_6)$-alkyl, O—$(C_1-C_6)$-alkyl, S—$(C_1-C_6)$-alkyl, S(O)—$(C_1-C_6)$-alkyl and $S(O)_2$—$(C_1-C_6)$-alkyl;
R25 is H;
R3 is $(C_2-C_{10})$-alkenyl
R4 and R5 are each independently H or $((C_1-C_6)$-alkyl;
R11, R12, R13, R14, R15 and R16 are each H;
m is 0; and
n is 0 or 1;
or a pharmaceutically acceptable salt thereof.

2. A pharmaceutical composition comprising the compound as recited in claim 1 formulated as a pharmaceutical formulation further comprising with pharmacologically acceptable carriers, inert bulking agents, solvents, excipients, stabilizing agents, diluents, tabletting agents, dissolution agents, penetration enhancers, flavor agents and fillers for administration to a patient in need thereof.

3. The pharmaceutical composition as recited in claim 2 further comprising at least one additional active ingredient.

4. The pharmaceutical composition as recited in claim 3 wherein said additional active ingredient is selected from the group consisting of one or more anti-diabetics, active hypoglycemic ingredients, HMG-CoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein(a) antagonists, lipase inhibitors, insulins, sulfonylureas, biguanides, meglitinides, thiazolidinediones, α-glucosidase inhibitors, active ingredients which act on the ATP-dependent potassium channel of the beta cells, CART agonists, NPY agonists, MC4 agonists, orexin agonists, H3 agonists, TNF agonists, CRF agonists, CRF BP antagonists, urocortin agonists, β agonists, CB1 receptor antagonists, MSH (melanocyte-stimulating hormone) agonists, CCK agonists, serotonin reuptake inhibitors, mixed serotonin and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists (bromocriptin, doprexin), lipase/amylase inhibitors, PPAR modulators, RXR modulators or TR-β agonists and amphetamines.

* * * * *

UNITED STATES PATENT AND TRADEMARK OFFICE
CERTIFICATE OF CORRECTION

PATENT NO. : 7,795,445 B2
APPLICATION NO. : 11/855221
DATED : September 14, 2010
INVENTOR(S) : Elisabeth Defossa et al.

It is certified that error appears in the above-identified patent and that said Letters Patent is hereby corrected as shown below:

In column 3, line 48, delete "alkylen" and insert -- alkylene --, therefor.

In column 5, line 20, delete "alkylen" and insert -- alkylene --, therefor.

In column 6, line 53, delete "alkylen" and insert -- alkylene --, therefor.

In column 9, line 1, delete "$(CH_2)_r$-aryl," and insert -- $(CH_2)_n$-aryl, --, therefor.

In column 11, line 60, delete "$(CH_2)_r$-aryl," and insert -- $(CH_2)_n$-aryl, --, therefor.

In column 12, line 10, delete "benzimidazalinyl," and insert -- benzimidazolinyl, --, therefor.

In column 12, line 27, delete "H-1,2,5" and insert -- 6H-1,2,5 --, therefor.

In column 13, line 13, delete "$(CH_2)_r$-aryl," and insert -- $(CH_2)_n$-aryl, --, therefor.

In column 17, line 62-63, delete "dexamphatamine" and insert -- dexamphetamine --, therefor.

In column 20, line 38, delete "$R^4$ or $R^5$" and insert -- R4 or R5 --, therefor.

In column 20, line 39, delete "$NR^4R^5$" and insert -- NR4R5 --, therefor.

In column 25, line 31, in claim 2, after "comprising" delete "with".

In column 26, line 22, in claim 4, delete "β" and insert -- β3 --, therefor.

In column 26, line 28, in claim 4, delete "bromocriptin," and insert -- bromocriptine, --, therefor.

Signed and Sealed this
Twenty-fourth Day of January, 2012

David J. Kappos
*Director of the United States Patent and Trademark Office*